United States Patent
Pendergast, Jr. et al.

(10) Patent No.: US 9,000,243 B2
(45) Date of Patent: Apr. 7, 2015

(54) PROCESS FOR SEPARATING CHLORINATED METHANES

(75) Inventors: John G Pendergast, Jr., Lake Jackson, TX (US); William S. White, Baton Rouge, LA (US); Anthony R. Avilla, Lake Jackson, TX (US); Thomas U Luebbe, Stade (DE)

(73) Assignee: Dow Global Technologies LLC, Midland, MI (US)

( * ) Notice: Subject to any disclaimer, the term of this patent is extended or adjusted under 35 U.S.C. 154(b) by 177 days.

(21) Appl. No.: 13/089,635

(22) Filed: Apr. 19, 2011

(65) Prior Publication Data

US 2011/0257445 A1 Oct. 20, 2011

Related U.S. Application Data

(60) Provisional application No. 61/325,562, filed on Apr. 19, 2010.

(51) Int. Cl.
| | |
|---|---|
| *C07C 17/38* | (2006.01) |
| *C07C 17/383* | (2006.01) |
| *B01D 3/14* | (2006.01) |
| *C07C 17/00* | (2006.01) |
| *C07C 19/00* | (2006.01) |
| *C07C 21/00* | (2006.01) |
| *C07C 23/00* | (2006.01) |

(52) U.S. Cl.
CPC .............. *C07C 17/383* (2013.01); *B01D 3/141* (2013.01)

(58) Field of Classification Search
CPC combination set(s) only.
See application file for complete search history.

(56) References Cited

U.S. PATENT DOCUMENTS

| | | | |
|---|---|---|---|
| 2,160,574 A | 5/1939 | Hennig et al. | |
| 2,276,166 A * | 3/1942 | Dachlauer et al. | 204/158.11 |
| 2,305,821 A | 12/1942 | Wimmer | |
| 2,727,076 A | 12/1955 | Warren | |
| 2,919,296 A | 3/1957 | Thermet et al. | |
| 3,363,010 A | 1/1968 | Schwarzenbek | |
| 3,454,660 A | 7/1969 | Chuffart | |
| 3,928,479 A | 12/1975 | Riemenschneider et al. | |
| 4,211,728 A | 7/1980 | Guerin | |
| 4,306,092 A | 12/1981 | Opavsky et al. | |
| 4,322,570 A | 3/1982 | de Klein | |
| 5,196,618 A | 3/1993 | Okon et al. | |
| 2007/0227875 A1 | 10/2007 | Kammerhofer | |
| 2009/0139852 A1 | 6/2009 | VanNuland et al. | |
| 2011/0087055 A1* | 4/2011 | Tirtowidjojo et al. | 570/159 |

FOREIGN PATENT DOCUMENTS

| | | |
|---|---|---|
| CA | 1242309 A1 | 9/1988 |
| WO | 2005110573 A1 | 11/2005 |

OTHER PUBLICATIONS

Shultz et al. CEP Magazine, May 2002, pp. 64-71.*

(Continued)

*Primary Examiner* — Clinton Brooks
(74) *Attorney, Agent, or Firm* — Susan M. Zerull; KSJLAW, LLC

(57) ABSTRACT

The present invention relates to a process for separating chlorinated methanes utilizing a dividing wall column. Processes and manufacturing assemblies for generating chlorinated methanes are also provided, as are processes for producing products utilizing the chlorinated methanes produced and/or separated utilizing the present process(es) and/or assemblies.

6 Claims, 2 Drawing Sheets

(56) References Cited

OTHER PUBLICATIONS

International Search Report and Written Opinion, PCT/US2009/042055, mailed Jun. 9, 2011.

Manfred Baerns et al., "Technische Chemie", Wiley, VCH Verlag GmbH & Co. KGaA, XP002639024, ISBN: 3-527-31000-2, pp. 589-591, 2003.

Dejanovic I et al., "Dividing Wall Column—A Breakhrough towards sustainable distilling" Chemical Engineering and Processing, Elsevier, vol. 49 (2010) pp. 559-580.

Wu, Jufang et al., "The separation of chloromethane mixtures and the recovery of dichloromethane, chloroform and carbon tetrachloride by adtivated carbon fibre", Absorption Science & Technology, vol. 20, 2002, pp. 169-177.

\* cited by examiner

PROCESS FOR SEPARATING CHLORINATED METHANES

FIELD

The present invention relates to a process for separating chlorinated methanes utilizing a dividing wall column. Processes for generating chlorinated methanes are also provided, as are processes for producing products utilizing the chlorinated methanes produced and/or separated utilizing the present process(es).

BACKGROUND

Many, if not all, chemical processes do not result in a purified end product, but rather, typically produce a family of products, or at least a single product that must be further purified to a saleable form. In many such processes, the additional products and/or byproducts produced typically have very similar chemical properties so that separation of the desired end product(s) can be difficult to perform. Suitable separation techniques can also be expensive—conventional distillation is known to be costly in time, energy, space and equipment requirements. Further, in order to provide multiple end products, multiple distillations may typically be required. If continuous processing is desired, multiple separation devices are typically purchased, installed and powered.

As but one example, processes for the production of chlorinated methanes do not produce one product, but rather, produce dichloromethane, chloroform and carbon tetrachloride. Each of these may have end product uses, but in order to be useable for such purposes, each must be dewatered, separated and purified from the product family. Conventional processes for producing chlorinated methanes thus typically include multiple components devoted to dewatering, i.e., a condensation train typically comprising at least two distillation units, and/or separating reaction products, i.e., a distillation train typically comprising at least two distillation units, to arrive at commercially acceptable end products. The overall process footprint and cost of operation of these conventional processes is significant and can become prohibitive.

Desirably, a process and apparatus for the production of chloromethanes would be provided that can minimize energy, material and space costs, while also minimizing any separation/purification costs associated with the use of any such process/apparatus in producing a product. As such, the commercial applicability of such a process/apparatus would be optimized.

BRIEF DESCRIPTION

The present invention provides such processes. More particularly, the present invention provides processes for separating at least two chlorinated methanes within a process stream. The processes make use of a dividing wall column, so that a more efficient separation than can be achieved with other types of separation units. Fewer separation units, or separations, are required to arrive at one or more commercially acceptable end-products and time, space, capital, and energy cost savings are provided.

In one aspect then, there is provided a process for the separation of a process stream comprising at least two chlorinated methanes. The process comprises providing a process stream comprising at least two chlorinated methanes to a dividing wall column so that the dividing wall column separates the at least two chlorinated methanes. The process stream may comprise dichloromethane, chloroform, carbon tetrachloride or combinations of two of these. In some embodiments, the dividing wall column may be provided with a side rectifier in a bottom portion thereof, so that trace intermediate components, such as those comprising bromine, may also be removed from the process stream.

The cost savings provided by the separation process provided herein may be leveraged by incorporating the separation process into a process for producing chlorinated methanes. More particularly, utilization of the present separation process within a process for producing chlorinated methanes can reduce the pieces of equipment required in the production process. Even more particularly, the separation process provided herein may replace, in whole or in part, the distillation segment typically included in a conventional process for the production of chlorinated methanes.

And so, there is also provided a manufacturing assembly for the production of chlorinated methanes. The assembly comprises a reactor, a condensation segment, and a distillation segment, wherein the distillation segment comprises a dividing wall column. The distillation segment may additionally comprise a distillation column in addition to the dividing wall column, i.e., the distillation segment of the present assembly utilizes at least one less distillation column than a distillation segment utilized in conventional chloromethane processes, which utilizes two distillation columns.

In a further aspect, the present invention provides a process for the production of chlorinated methanes. The process comprises generating a process stream comprising at least two chlorinated methanes; and providing the process stream to a dividing wall column. A first, second and third process stream may be recovered from the divided wall column, and will desirably consist of dichloromethane, chloroform and carbon tetrachloride, respectively. In some embodiments, the dividing wall column may comprise a side-rectifier in a bottom portion thereof, so that trace intermediate components may also be removed from the process stream, if desired. Brominated compounds, for example, may be removed utilizing the side-rectifier in embodiments wherein the same is provided.

BRIEF DESCRIPTION OF THE DRAWINGS

These and other features, aspects, and advantages of the present invention will become better understood when the following detailed description is read with reference to the accompanying drawings, wherein.

DETAILED DESCRIPTION

Figure 1:
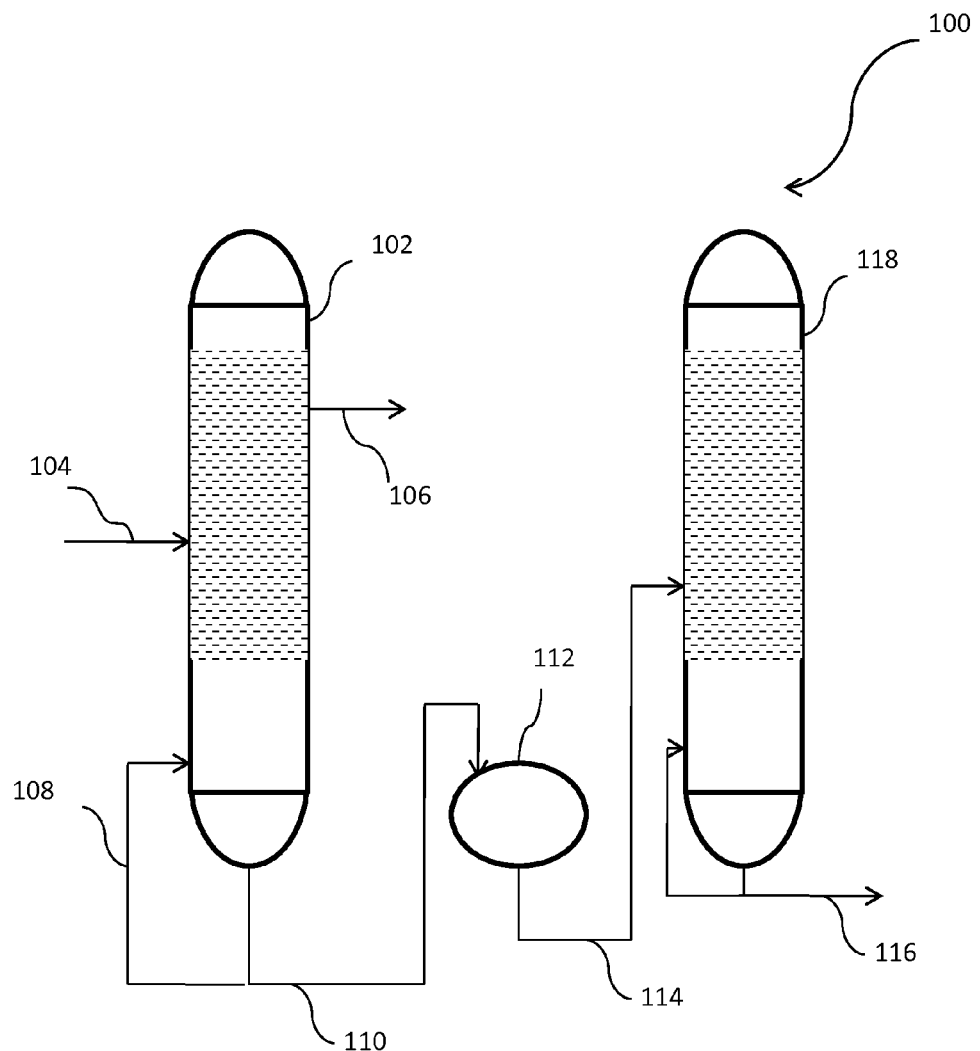
FIG. 1 is a schematic diagram of a conventional distillation segment for chlorinated methanes.

The present specification provides certain definitions and methods to better define the present invention and to guide those of ordinary skill in the art in the practice of the present invention. Provision, or lack of the provision, of a definition for a particular term or phrase is not meant to imply any particular importance, or lack thereof. Rather, and unless otherwise noted, terms are to be understood according to conventional usage by those of ordinary skill in the relevant art.

The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation.

If ranges are disclosed, the endpoints of all ranges directed to the same component or property are inclusive and independently combinable (e.g., ranges of "up to about 25 wt. %, or, more specifically, about 5 wt. % to about 20 wt. %," is inclusive of the endpoints and all intermediate values of the ranges of "about 5 wt. % to about 25 wt. %," etc.). The modifier "about" used in connection with a quantity is inclusive of the stated value and has the meaning dictated by the context (e.g., includes the degree of error associated with measurement of the particular quantity). Unless otherwise defined, all percents are provided as weight percents.

Processes for the separation of chlorinated methanes are provided herein. The present processes advantageously utilize dividing wall column, and so, at least two chlorinated methanes, and preferably three chlorinated methanes, can be separated more efficiently than when conventional separation processes are utilized. For example, one dividing wall column may typically replace at least two conventional distillation columns, and so, capital cost savings are provided in that only one dividing wall column needs be purchased rather than two distillation columns. Energy savings are also provided, since the energy costs associated with operating one dividing wall column are significantly less than the energy costs associated with operating two conventional distillation columns. Finally, the footprint required for one dividing wall column is significantly less than the footprint required for the at least distillation columns that it can replace, and manufacturing space is thus saved.

Dividing wall columns are distillation columns with a vertical dividing wall which divides the column in the longitudinal direction in its central region and that prevents cross-mixing of liquid and vapor streams in that region. The feed is provided to the central region of the column. A high boiler fraction is discharged from the bottom of the column, a low boiler faction is discharged from the top of the column and a medium boiler fraction is discharged from the central region of the column.

While such columns are known for the separation of multi-component mixtures, they have not been utilized for the separation of chlorinated methanes. For older processes, the investment, of capital, space and training, has already been made in the conventional distillation columns/processes. Until replacement is required, it may not be economically sound to do so and consideration of alternatives is not undertaken. Further, had such consideration taken place, and prior to the present invention, those of ordinary skill in the art apparently concluded that it would have been impossible, or in the least, prohibitively expensive in cost and space, to provide a dividing wall column capable of separating chlorinated methanes due to the closeness of the boiling points of dichloromethane, chloroform and carbon tetrachloride.

More particularly, a processing stream comprising chlorinated methanes can be separated into at least two components thereof utilizing a dividing wall column comprising from about 100 to about 150 equilibrium stages, preferably from about 110 to about 140 equilibrium stages, and more preferably about 120 to about 130 equilibrium stages. As those of ordinary skill in the art are aware, the stages in a dividing wall column may be provided by trays, packing, or combinations thereof.

In some embodiments, the dividing wall column may be provided with a side rectifier, or side stripper, so that further separations are possible. For example, many processes for the production of chlorinated methanes may introduce, or supplies of chlorinated methanes may comprise, brominated contaminants. Such contaminants, although difficult to remove via other processes, may readily be removed with a dividing wall column provided with a side stripper or rectifier. As those of ordinary skill in the art are aware, a side-rectifier or side-stripper extracts of a portion of the dividing wall column's flow into a separate unit that is equipped with either a separate heat or condensing source. In the case of the side rectifier, the product that is removed is rectified, or enriched in light components, and some fraction of these intermediate light components are removed from the system.

The dividing wall column may have one vertical wall, or more than one. If more than one, the vertical walls may have the same, or different lengths. Further, the vertical wall need not be exactly vertical, but can deviate from vertical by 5 degrees, 10 degrees or even up to 20 degrees, from vertical. The wall(s) is/are desirably long enough to traverse substantially all of the horizontally arranged separating trays of the column, and may desirably begin from one of the lower most stages to one of the upper most stages. Finally, the wall(s) may comprise any suitable materials, typically, dividing walls comprise alloyed or non-alloyed stainless steel.

The present processes comprise providing a process stream comprising at least two chlorinated methanes to the dividing wall column. At least two chlorinated methanes, or more, may be separated and the separation affected substantially simultaneously. Separations of, e.g., substantially pure fractions of chloroform ($CHCl_3$, CAS 67-66-3) and carbon tetrachloride ($CCl_4$, CAS 56-23-5), or dichloromethane ($CH_2Cl_2$, CAS 75-09-2), chloroform and carbon tetrachloride, are expected to be provided from a process stream comprising the same, utilizing the present process.

The present process of separating chlorinated methanes may be utilized as a stand-alone process, or, may be operatively coupled with one or more additional processes. For example, the present processes may be coupled to additional separation processes, so that additional separations can be performed on the separated chlorinated methanes provided by the present process. For example, in those embodiments wherein a process stream comprising dichloromethane, chloroform and carbon tetrachloride is provided to a dividing wall column, a bottom fraction comprising about 5 wt % chloroform and about 95 wt % carbon tetrachloride may be obtained. Such a fraction may be subjected to a further separation technique so that substantially pure fractions, i.e., comprising only trace amounts of impurities, of chloroform and carbon tetrachloride are provided.

In such embodiments, the bottom fraction, or whatever fraction is desirably further purified, may be subjected to conventional distillation, or, may be provided to an additional dividing wall column. Those of ordinary skill in the art of chemical engineering are capable of determining appropriate conventional distillation parameters to affect the desired separation via conventional distillation. If desirably separated by an additional dividing wall column, the additional dividing wall column would be operated at approximately the same pressure, or within from about one to five atmospheres, and with about 140 to about 190 equilibrium stages, preferably from about 150 to about 180 equilibrium stages, and more preferably about 160 to about 170 equilibrium stages.

The advantages provided by the processes described herein may be further understood with reference to FIG. 1, wherein one example of a conventional distillation segment for a process for producing chlorinated methanes is illustrated. More specifically, distillation train 100 comprises two distillation columns 102 and 118.

In typical operation, feedstream 104 may be provided to distillation column 102 from any source. For example, feedstream 104 may be delivered from a distillation column (not shown) within a condensation manufacturing segment, or "train" (not shown). Such condensation trains may typically be utilized to remove a large portion, or substantially all, of any water within the processing stream. In such embodiments, when processing stream 104 is provided to distillation column 102, it is thus substantially free of water, and may comprise, for example from about 10 wt % to about 90 wt % dichloromethane, from about 10 wt % to about 90 wt % chloroform and from about 1 wt % to about 10 wt % carbon tetrachloride.

Distillation column 102 would typically be operated with a top temperature of about 85° C., a bottom temperature of about 125° C. and at a pressure of about 45 psig (4.1 bar absolute). At these conditions, process stream 106 would be expected to comprise about 99.9999% dichloromethane and 10 parts per million chloroform, while bottoms stream 110 would be expected to comprise about 91% chloroform, about 9% carbon tetrachloride and about 10 ppm of dichloromethane. A portion 108 of process stream 110 would be diverted and recycled to distillation column 102 while the remainder of process stream 110 would be directed to distillation column 118, via heater/pump 112.

Process stream 114 would thus be expected to comprise a pressure of about 2 to 3 bar absolute and a temperature of from about 120° C. to about 130° C. prior to being introduced into distillation column 118. Distillation column 118 may desirably be at a pressure of about 2 to 2.5 bar absolute and have a top temperature of about 65° C. and a bottom temperature of about 125° C. A portion of process stream 116 may typically be recycled to distillation column 118, while the remainder, comprising about 2 to 5% chloroform and about 95 to 98% carbon tetrachloride may typically be subjected to further purification/processing techniques.

The manufacturing footprint required for installation of distillation columns 102 and 118 would be expected to be about 400 sq ft per tower or 800 sq feet for both installations.

Figure 2:
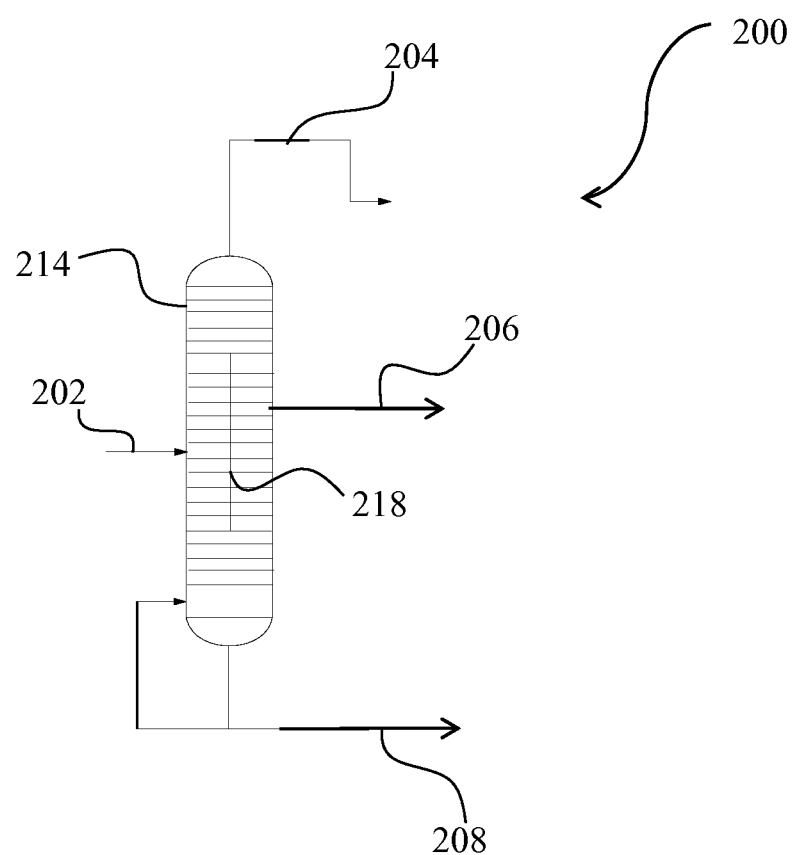
FIG. 2 is a schematic diagram of one embodiment of a distillation segment according to the present invention.

In contrast, a dividing wall column as utilized in the present processes and assembly is illustrated in FIG. 2. More specifically, distillation segment 200 comprises dividing wall column 214. Dividing wall column 214 comprises vertical wall 218 that extends through a midrange of dividing wall column 214.

In typical operation, feedstream 202 may be provided to dividing wall column 214 from any source. As described in connection with FIG. 1, feedstream 202 may be delivered from a condensation manufacturing segment. As such, feedstream 202 would be expected to comprise from about 10 wt % to about 90 wt % dichloromethane, from about 10 wt % to about 90 wt % chloroform and from about 1 wt % to about 10 wt % carbon tetrachloride.

Dividing wall column 214 would typically be operated at a top temperature of from about 65° C. to about 70° C., or of about 68° C., and at a bottom temperature of from about 120° C. to about 130° C., or of about 125° C., and at a pressure of about 2 to 2.5 bar absolute. At these conditions, upper process stream 204 would be expected to comprise substantially pure dichloromethane, with trace amounts of chloroform and carbon tetrachloride, while middle process stream 206 would be expected to comprise substantially pure chloroform, with only trace amounts of dichloromethane and carbon tetrachloride. Bottoms process stream 208 would be expected to comprise about 95 wt % carbon tetrachloride, 5 wt % chloroform and only trace amounts of dichloromethane.

The manufacturing footprint required for installation of distillation segment 200 would be expected to be about 400 sq ft.

The utilization of a dividing wall column in the distillation segment of a manufacturing assembly for chlorinated methanes thus provides significant footprint savings. And so, there is also provided herein a manufacturing assembly for chlorinated methanes comprising a suitable reactor, a condensation segment, and a distillation segment, wherein the distillation segment comprises a dividing wall column and no more than three distillation columns, preferably no more than two distillation columns. The dividing wall column will desirably comprise from about 100 to 150 equilibrium stages, preferably from about 110 to 140 equilibrium stages, and more preferably from about 120 to about 130 equilibrium stages. The stages may be provided by trays, packing, or combinations thereof.

Since the processes described herein utilize a dividing wall column, the processes may be carried out substantially continuously and separation of the chlorinated methanes may be affected substantially simultaneously, if desired. The present processes thus can exhibit greater separation efficiency than conventional distillation columns, and in some embodiments, even conventional distillation columns having substantially the same number of separation stages/trays. The present processes thus provide separated chlorinated methanes having a high degree of purity, while at the same time providing a reduction in capital and operating expense. Reduced downtime and cleaning expenses may also be provided by the present processes.

The separation process provided herein may be incorporated into processes for the production of chlorinated methanes, and the advantages provided by the separation process thus leveraged. Typical processes for the production of chlorinated methanes may include reacting monochloromethane with chlorine, and may provide process streams comprising, e.g., dichloromethane, chloroform, carbon tetrachloride or combinations of these.

The chlorinated methanes separated and/or produced by the processes described herein may be utilized in downstream processes to provide additional products. For example, dichloroform and chloroform may be used to produce coatings, adhesives, drycleaning chemicals, fluorocarbons, refrigerants, paints, paint strippers, urethane foams, pharmaceuticals, etc.

The following examples are set forth for the purpose of illustrating the invention; but these examples are not intended to limit the invention in any manner. One skilled in the art will recognize a variety of substitutions and modifications of the examples that will fall within the scope of the invention.

EXAMPLE 1

In this example, a feedstream comprising chlorinated methanes and having a flow rate of about 25000 kg/hr is provided to a dividing wall column similar to that shown in FIG. 2.

More particularly, the feedstream comprises about 78 wt % dichloromethane, about 19 wt % chloroform, and about 3 wt % carbon tetrachloride. The dividing wall column inlet temperature is about 125° C., the top temperature is about 68° C. and the column is at a pressure of about 2 bar absolute.

Upon exit from the dividing wall column 214, the upper product stream (204 in FIG. 2) has a mass flow rate of about 20250 kg/hr and comprises about substantially pure dichloromethane, having less than 10 ppm chloroform and only trace amounts of carbon tetrachloride. The mid product stream (206 in FIG. 2) has a mass flow rate of about 4150 kg/hr and comprises substantially pure chloroform, having less than 10 ppm dichloromethane and less than 10 ppm carbon tetrachloride. Finally, the bottom product stream (208 in FIG. 2) has a mass flow rate of about 400 kg/hr and comprises 95 wt % carbon tetrachloride, 5 wt % chloroform and only trace amounts of dichloromethane.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A process for the separation of a process stream comprising carbon tetrachloride, chloroform and dichloromethane comprising providing the process stream to a dividing wall column comprising from about 100 to about 150 equilibrium stages and operated with a top temperature of from about 65° C. to about 70° C. and a bottom temperature of from about 120° C. to about 130° C., wherein the dividing wall column comprises a side-rectifier in a bottom portion of the dividing wall column and the process further comprises removing intermediate components from the process stream utilizing the side rectifier, and wherein the dividing wall column separates the carbon tetrachloride from the chloroform and/or dichloromethane.

2. The process of claim 1, wherein the intermediate components are brominated.

3. A process for the production of chlorinated methanes comprising
generating a process stream comprising carbon tetrachloride, chloroform and dichloromethane; and
providing the process stream to a dividing wall column comprising from about 100 to about 150 equilibrium stages and operated with a top temperature of from about 65° C. to about 70° C. and a bottom temperature of from about 120° C. to about 130° C.; wherein the dividing wall column comprises a side-rectifier in a bottom portion of the dividing wall column and the process further comprises removing intermediate components from the process stream utilizing the side rectifier, and wherein the dividing wall column separates the carbon tetrachloride from the chloroform and/or dichloromethane.

4. The process of claim 3, further comprising recovering a stream of about 95 wt % carbon tetrachloride and a stream of about 5 wt % of chloroform or dichloromethane.

5. The process of claim 3, further comprising recovering a stream of about 95 wt % carbon tetrachloride and a stream of about 5 wt % of chloroform and dichloromethane.

6. The process of claim 3, wherein the intermediate components are brominated.

* * * * *